United States Patent [19]

Oka et al.

[11] Patent Number: 4,521,607
[45] Date of Patent: Jun. 4, 1985

[54] CHROMANYL GLYCINES

[75] Inventors: Yoshikazu Oka, Kawanishi; Kohei Nishikawa, Kyoto; Akio Miyake, Hirakata, all of Japan

[73] Assignee: Takeda Chemical Industries, Ltd., Osaka, Japan

[21] Appl. No.: 365,038

[22] Filed: Apr. 2, 1982

Related U.S. Application Data

[62] Division of Ser. No. 238,821, Feb. 27, 1981, abandoned.

[51] Int. Cl.³ .................. C07D 307/82; C07D 311/68
[52] U.S. Cl. ...................................... 549/39; 549/349; 549/361; 549/433; 549/355; 549/404; 549/467; 549/359; 560/10; 560/427
[58] Field of Search ............... 549/200, 349, 361, 433, 549/30, 355, 404, 467, 359, 35; 560/10, 427

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,116,962 | 9/1978 | Ondetti et al. | 546/349 |
| 4,256,761 | 3/1981 | Suh et al. | 424/282 |

FOREIGN PATENT DOCUMENTS 2024814  1/1980  United Kingdom ............... 546/349

*Primary Examiner*—Henry R. Jiles
*Assistant Examiner*—Robert C. Whittenbaugh
*Attorney, Agent, or Firm*—Wegner & Bretschneider

[57] ABSTRACT

New bicyclic compounds, inclusive of salts thereof, of the formula:

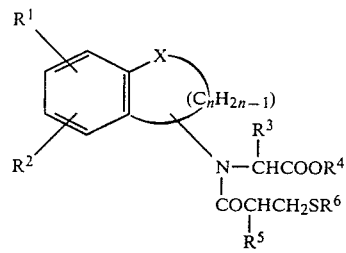

wherein $R^1$ and $R^2$, which may be the same or different, each represent hydrogen, halogen, lower alkyl, hydroxyl, lower alkyloxy or aralkyloxy, or $R^1$ and $R^2$ jointly represent lower alkylenedioxy; $R^3$ and $R^4$ each represent hydrogen or lower alkyl; $R^5$ represents hydrogen, lower alkyl or —$CH_2SR^7$ ($R^7$ represents hydrogen or acyl); $R^6$ represents hydrogen or acyl, or $R^6$ and $R^7$ jointly represent a single bond; X represents —$CH_2$—, —O— or >N—$R^8$ ($R^8$ represents hydrogen, acyl or lower alkyl); and n represents 2, 3 or 4, have inhibitory activities of angiotensin converting enzyme and bradykinin decomposing enzyme, and are useful as antihypertensive agents.

15 Claims, No Drawings

CHROMANYL GLYCINES

This application is a divisional of application Ser. No. 238,821 filed Feb. 27, 1981, now abandoned.

This invention relates to novel bicyclic compounds which are useful as pharmaceuticals and a process for producing the same.

More particularly, the present invention relates to bicyclic compounds, inclusive of their salts thereof, of the formula:

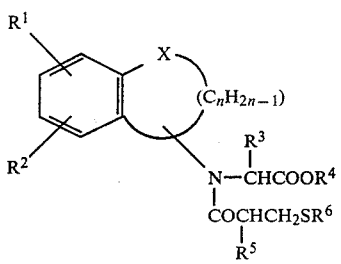

wherein $R^1$ and $R^2$, which may be the same or different, each represent hydrogen, halogen, lower alkyl, hydroxyl, lower alkyloxy or aralkyloxy, or $R^1$ and $R^2$ jointly represent lower alkylenedioxy; $R^3$ and $R^4$ each represent hydrogen or lower alkyl; $r^5$ represents hydrogen, lower alkyl or $-CH_2SR^7$ ($R^7$ represents hydrogen or acyl); $R^6$ represents hydrogen or acyl, or $R^6$ and $R^7$ jointly represent a single bond; X represents $-CH_2-$, $-O-$ or $>N-R^8$ ($R^8$ represents hydrogen, acyl or lower alkyl); and n represents 2, 3 or 4, and a process for producing the same.

Referring to the above formula (I), the halogen represented by $R^1$ and $R^2$ includes, for example, chlorine, bromine, iodine and fluorine, the lower alkyl represented by $R^1$ and $R^2$ includes, for example, alkyl having 1 to 4 carbon atoms (e.g. methyl, ethyl, propyl, isopropyl, butyl, isobutyl or tert-butyl), the lower alkyloxy represented by $R^1$ and $R^2$ includes, for example, alkyloxy having 1 to 4 carbon atoms (e.g. methoxy, ethoxy, propoxy, isopropoxy, butoxy or isobutoxy), the aralkyloxy group represented by $R^1$ and $R^2$ includes, for example, aralkyloxy having 7 to 9 carbon atoms (e.g. benzyloxy, phenethyloxy, α-methylbenzyloxy) and the lower alkylenedioxy formed by linking $R^1$ and $R^2$ includes alkylenedioxy having 1 to 4 carbon atoms (e.g. methylenedioxy, ethylenedioxy, ethylidenedioxy, isopropylidenedioxy) and the like. The lower alkyl represented by $R^3$, $R^4$, $R^5$ and $R^8$ includes the same lower alkyl groups as those represented by $R^1$ and $R^2$. The acyl represented by $R^6$ and $R^7$ includes, for example, an acyl derived from a carboxylic acid such as lower alkanoyl having 2 to 4 carbon atoms (e.g., acetyl, propionyl, butyryl, isobutyryl), aroyl (e.g., benzoyl) and the like. The acyl represented by $R^8$ includes the same lower alkanoyl groups as those represented by $R^6$ and $R^7$.

Further, when $R^6$ and $R^7$ jointly represent a single bond, the compound (I) is represented by a compound having a dithiolan ring of the formula:

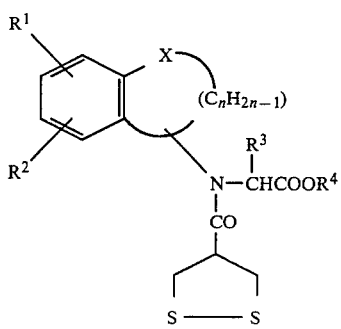

wherein all symbols are as defined above.

In the compounds of the present invention, preferred embodiment are compounds of the formula (I) wherein $R^1$ and $R^2$ independently represent hydrogen, halogen, $C_{1-4}$alkyl, hydroxyl, $C_{1-4}$alkyloxy or $C_{7-7}$aralkyloxy, or $R^1$ and $R^2$ jointly represent $C_{1-4}$alkylenedioxy; $R^3$ and $R^4$ independently represent hydrogen or $C_{1-4}$alkyl; $R^5$ is hydrogen, $C_{1-4}$alkyl or $-CH_2SR^7$ wherein $R^7$ is hydrogen, $C_{2-4}$alkanoyl or benzoyl; $R^6$ is hydrogen, $C_{2-4}$alkanoyl or benzoyl, or $R^6$ and $R^7$ jointly represent a single bond; X is $-CH_2-$, $-O-$ or $>N-R^8$ wherein $R^8$ is hydrogen, $C_{2-4}$alkanoyl or $C_{1-4}$alkyl; and n is 2, 3 or 4, and their pharmaceutically acceptable salts.

The compounds (I) of the present invention can be produced by, for example, reacting a compound of the formula:

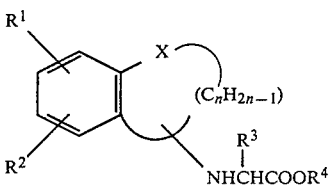

[wherein all the symbols are as defined above] with a compound represented by the formula:

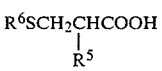

[wherein $R^5$ and $R^6$ are as defined above] or a reactive derivative thereof at the carboxyl function.

The reactive derivative of the compound (III) at the carboxyl function used in the above reaction between the compounds (II) and (III) includes a derivative, for example, an acid halide such as acid chloride, acid bromide and the like, an acid anhydride obtained by dehydrating one molecule of water from two molecules of the compound (III), a mixed anhydride of the compound (III) wherein the hydrogen atom of carboxyl is substituted with, for example, ethoxycarbonyl, isobutoxycarbonyl, benzyloxycarbonyl, etc.

The reaction can be generally carried out in a suitable solvent and any solvent can be used so long as it does not adversely affect the reaction. When the compound (III) is used per se without converting into its reactive derivative, the reaction is advantageously conducted in the presence of a dehydrating agent, for example, dicyclohexylcarbodiimide, carbonyldiimidazole and the like. When an acid halide is used as said reactive derivative, the reaction can also be conducted in the presence of a base such as pyridine, picoline, triethylamine, sodium hydroxide, sodium bicarbonate, sodium carbonate, etc. The reaction can be generally carried out at a temperature in the range of from about −20° C. to about +150° C. and in most instances, it proceeds sufficiently at ambient temperature.

The compound of the formula (I) wherein $R^6$ and/or $R^7$ is hydrogen can also be prepared by hydrolyzing the compound (I) wherein $R^6$ and/or $R^7$ is acyl.

The hydrolysis is generally effected in water, an organic solvent or a mixture of these solvents in the absence or presence of an acid, for example, hydrochloric acid, sulfuric acid, nitric acid, phosphoric acid, acetic acid, trifluoroacetic acid, benzensulfonic acid, methanesulfonic acid, p-toluenesulfonic acid and the like, or a base, for example, ammonia, sodium bicarbonate, triethylamine, pyridine, picoline and the like. The hydrolysis is generally conducted at a temperature ranging from about −20° C. to about +150° C., but, in most instances, it proceeds sufficiently at ambient temperature. In this reaction, the carboxylic acid ester of the compound (I) may be simultaneously hydrolyzed, but when the ester form is desired it can be easily prepared by subjecting the compound obtained after hydrolysis to a conventional esterification procedure.

Contrary to the above, the compound (I) wherein $R^6$ and/or $R^7$ is acyl can also be prepared by acylating the compound (I) wherein $R^6$ and/or $R^7$ is hydrogen. The above acylation can be carried out in the same manner as described for the acylation of the compound (II).

Further, the compound of the formula (I) above can also be produced by reacting a compound represented by the formula:

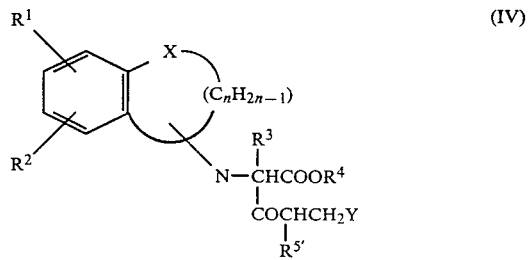

(IV)

[wherein $R^{5'}$ represents hydrogen, lower alkyl or —CH$_2$Z; Y and Z each represent halogen or a group represented by $R^9SO_2O$— ($R^9$ is $C_{1-4}$alkyl, phenyl or p-tolyl) and the other symbols are as defined above], with a compound represented by the formula:

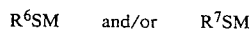

[wherein $R^6$ and $R^7$ are as defined above and M represents hydrogen or an alkali metal.]

In the above process, the lower alkyl represented by $R^{5'}$ in the formula (IV) corresponds to the lower alkyl of $R^5$, the halogen represented by Y and Z includes chlorine, bromine and iodine, and the alkali metal represented by M in the formulae (V) and (V') includes lithium, sodium, potassium and the like. The reaction is conducted in a suitable solvent with heating or cooling at a temperature ranging from about −20° C. to about +150° C. When M is hydrogen, the reaction may proceed advantageously in the presence of a base, for example, sodium hydroxide, potassium hydroxide, sodium carbonate, ammonia, pyridine, triethylamine and the like. When $R^6$ and $R^7$ are different from each other, the compounds (V) and (V') can be reacted simultaneously or in sequence with the compound (IV).

The compound of the formula (I) wherein $R^6$ and $R^7$ jointly represent a single bond, i.e., the compound represented by the formula (Ia) can also be prepared by oxidizing the compound of the formula (I) wherein $R^6$ and $R^7$ are hydrogen.

As the procedure of the above oxidation, there may be mentioned oxidation procedures using, for example, (1) air or oxygen, (2) halogen such as chlorine, bromine or iodine, (3) peroxides, for example, hydrogen peroxide, sodium peroxide, potassium peroxide, peracetic acid, perbenzoic acid, m-chloroperbenzoic acid, periodic acid, perchloric acid, potassium perchlorate, etc. (4) ferric compounds, for example, potassium ferricyanide, ferric chloride, etc., (5) sodium tetrathionate ($Na_2S_4O_6$), (6) sulfoxide compounds, for example, dimethylsulfoxide, etc., or (7) an oxidase.

In addition to the above procedures, any other procedures for oxidizing a mercaptan into a disulfide can be employed.

The above oxidation reaction is generally carried out in water, an organic solvent or a mixture thereof, and the organic solvent may be any type of solvent so long as it is capable of dissolving the starting materials and it does not adversely affect the reaction. The reaction temperature varied depending upon the oxidation procedure used, but is preferably from about −20° C. to about 100° C. and, in most instances, the reaction proceeds adequately at ambient temperature. Also, in order to promote the reaction, a suitable catalyst such as an acid (e.g. hydrochloric cid, sulfuric acid, acetic acid), a base (e.g. ammonia, sodium hydroxide, potassium hydroxide, sodium ethoxide, triethylamine), a metal ion (e.g. a sodium, potassium, calcium, iron, nickel or cobalt ion), silica gel, alumina, activated carbon or diatomaceous earth may be used. In this reaction, the compound (I) wherein $R^6$ and $R^7$ are hydrogen atoms as raw material can be used in the form of a salt at the carboxyl moiety and/or the mercapto moiety (for example, a sodium, potassium or magnesium salt, etc.).

The desired compound (I) thus obtained can be isolated from the reaction mixture by conventional separation and purification procedures, for example, extraction, concentration, neutralization, filtration, recrystallization, column chromatography, thin layer chromatography and the like. When $R^4$ represents hydrogen, the compound (I) can be isolated in the form of a free acid or a salt which includes a pharmaceutically acceptable salt such as a salt with an inorganic base (e.g. sodium salt, potassium salt, calcium salt, lithium salt, aluminum salt, magnesium salt, barium salt, ammonium salt, etc.) or an organic base addition salt (e.g. methylamine salt, diethylamine salt, triethylamine salt, dicyclohexylamine salt, dibenzylamine salt, hydrazine salt, hydralazine salt, guanidine salt, arginine salt, histidine salt, pyridinium salt, imidazolium salt, quinone salt, cinchonine salt, quinidine salt, cinchonidine salt, etc.). Also, the free acid (I) can be converted into an ester form by a conventional esterification procedure.

The compound represented by the formula (I) according to the present invention has 1 to 3 asymmetric carbons in the molecule and, therefore, may exist as 2 to 8 isomers. Each of these isomers as well as a mixture of these isomers are of course included within the scope of the present invention, and these isomers can be prepared separately if desired. That is, an optical isomer of the compound (I) may be obtained by conducting the above reaction using the corresponding optical isomer of either the starting material (II) or (III), the isomer being obtained by optical resolution previously conducted. When at least one of (II) and (III) is a racemate, the compound (I) may be generally obtained as a mixture of isomers, but, if desired, these isomers can be separated into each of the isomers in accordance with a usual optical resolution procedure, for example, a method comprising the formation of a salt with an optically active base (for example, cinchonine, cinchonidine, quinine, quinidine, etc.) or a method comprising chromatography, fractional recrystallization, etc.

The compounds of the present invention, i.e., the bicyclic compounds represented by the formula (I) and the salts thereof, exhibit inhibitory activities on angiotensin I converting enzyme, bradykinin decomposing enzyme (kininase) and encephalinase in animals, in particular, mammals and therefore are useful as drugs for dignosis, prevention or treatment of hypertension and as analgesic and analgesic-activity-protentiating agents. The compounds of the present invention are of low toxicity, well absorbed even on oral administration and highly stable. Therefore, when they are used as the above-mentioned drugs, they can safely be administered orally or parenterally, per se or in admixture with suitable pharmaceutically acceptable carriers, excipients or diluents in various pharmaceutical formulations such as powders, granules, tablets, capsules, injectable solutions, etc. While the dosage level generally varies depending upon the conditions of the diseases to be treated as well as the administration route used, for example, in the treatment of hypertension in adult human, the compounds may be administered orally at a single dose of about 0.02–20 mg/kg, preferably about 0.2–2 mg/kg, or intravenously at about 0.002–0.2 mg/kg, preferably about 0.02–0.2 mg/kg, about 2 to 5 times per day according to the conditions.

In the above-mentioned pharmaceutical uses, preferred embodiments among compounds (I) of the present invention are those compounds wherein X is methylene and n is 2, namely compounds having an indane ring structure, with the amino acid side chain being present preferably in the 2-position of the indane ring. Such compounds are represented by the following formula (I'):

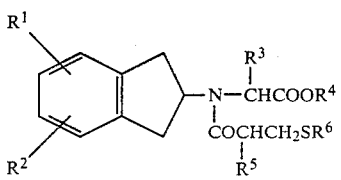

[wherein all the symbols are as defined above.]

With respect to the compounds of the above formula (I'), it is preferred that $R^1$ and $R^2$ are both hydrogen atoms or both methoxy groups (especially at the 5- and 6-positions), that $R^3$ and $R^4$ are hydrogen atoms, and that $R^5$ is methyl. When $R^5$ is methyl, it has preferably a S-configuration.

The starting compounds (II) in the present invention can be prepared, for example, (1) by reacting a cyclic ketone of the formula:

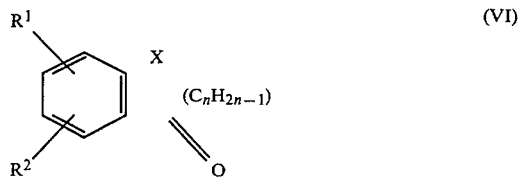

[wherein all the symbols are as defined above] with a compound of the formula:

[wherein $R^3$ and $R^4$ are as defined above] and reducing the resultant, so-called Schiff base; or (2) by reacting the cyclic ketone (VI) with benzylamine under a ruductive condition, reacting the resulting compound of the formula:

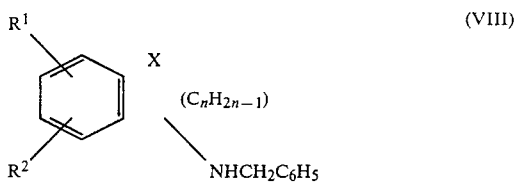

[wherein all the symbols are as defined above] with a compound of the formula:

[wherein $R^3$ and $R^4$ are as defined above and Y' is defined as Y in the formula (IV)] and then subjecting the resulting compound of the formula:

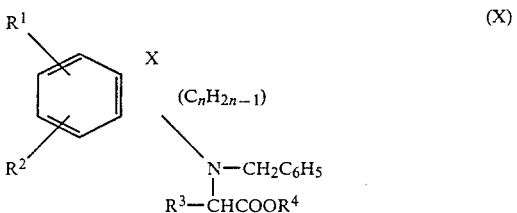

[wherein all the symbols are as defined above] to catalytic reduction; or (3) by reacting a compound of the formula:

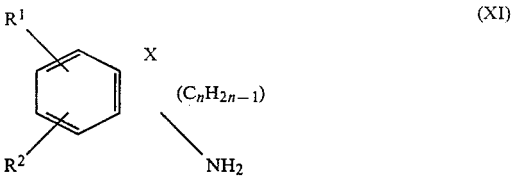

[wherein all the symbols are as defined above] with the compound (IX).

These methods for preparing compounds (II) will be illustrated in detail. Method (1) is carried out by first reacting compound (VI) with compound (VII) in an appropriate solvent to form a Schiff base and subjecting the Schiff base to reduction. As the solvent, there may be mentioned an organic solvent such as methanol, ethanol, dioxane, methylene chloride, chloroform, benzene or toluene, and the reaction may be generally carried out at a temperature within the range of about −10° C. to about +150° C. For advantageously accelerating the reaction, a catalyst (e.g. sulfuric acid or p-toluenesulfonic acid) or a dehydrating agent (e.g. anhydrous sodium sulfate, anhydrous magnesium sulfate or calcium chloride) may be added to the reaction mixture. It is also possible to advantageously promote the reaction by carrying out the reaction using a water-separating device. The Schiff base, as it is in the reaction mixture or after isolation in the conventional manner and redissolution in a solvent, is subjected to reduction. The reduction procedure may for example be catalytic reduction using as a catalyst such as platinum or palladium-carbon, or reduction using such a reducing agent as sodium borohydride or sodium cyanoborohydride. It is also possible to make the formation of the Schiff base and reduction thereof proceed simultaneously by making such reducing agent coexist in the reaction mixture of (VI) and (VII) from the beginning. The reaction of (IV) and benzylamine in Method (2), like the reaction of (VI) and (VII) in method (1), proceeds via a Schiff base. The reaction of (VIII) and (IX) is effected by maintaining both the reactants in an appropriate organic solvent at a temperature within the range of about −10° C. to about +200° C. In this case, such a base as potassium carbonate, sodium hydroxide, sodium hydrogen carbonate or pyridine may be made to coexist in the reaction system as a deacidifying agent for the purpose of accelerating the reaction. Compounds (X) produced by this reaction are debenzylated by catalytic reduction using, for example, palladium-carbon as a catalyst, to give compounds (II). The catalytic reduction is carried out at ordinary pressure or under pressure up to about 150 kg/cm² and at ordinary temperature to 150° C. Generally, the reaction proceeds in a satisfactory manner at ordinary temperature and pressure. The reaction of (XI) and (IX) in Method (3) may be carried out under the same conditions as for the reaction of (VIII) and (IX).

The present invention will be illustrated more detailedly by the following reference examples, examples, experiments and preparation examples, which, however, should by no means be construed as limitative of the present invention.

REFERENCE EXAMPLE 1

In 300 ml of benzene are dissolved 5,6-dimethoxy-1-indanone (19 g), benzylamine (12 g) and p-toluenesulfonic acid (5 g). The mixture is refluxed for 7 hours while removing the water formed in the reaction system by means of a water-separator. The insolubles are then filtered off, and the filtrate is concentrated by distilling the solvent off under reduced pressure. The residue is dissolved in 200 ml of methanol, and 5.0 g of sodium borohydride is added portionwise under ice cooling. After stirring at room temperature for 30 minutes, the reaction mixture is poured into 1 liter of ice-water and extracted with 500 ml of ethyl acetate. The extract is washed with water, dried, and evaporated to remove the ethyl acetate. To the residue are added 10 ml of 20% alcoholic hydrochloric acid and then 200 ml of ethyl ether. After allowing the mixture to stand at room temperature, the crystalline precipitates are collected by filtration to give 17 g of 1-benzylamino-5,6-dimethoxyindane hydrochloride as colorless needles. Melting point: 180°–182° C.

REFERENCE EXAMPLES 2–24

The compounds shown in Table 1 can be obtained in a similar reaction procedure to that described in Example 1, by employing, as the respective starting compounds, the corresponding cyclic ketone compounds.

TABLE 1

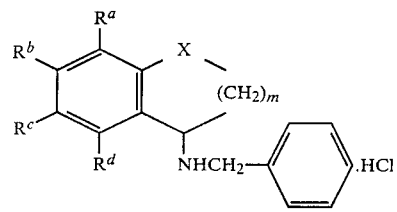

| Ref. No. | $R^a$ | $R^b$ | $R^c$ | $R^d$ | X | m | Melting Point(°C.) |
|---|---|---|---|---|---|---|---|
| 2 | OCH₃ | H | H | H | CH₂ | 1 | 198–200 |
| 3 | H | H | OCH₃ | H | CH₂ | 1 | 166–168 |
| 4 | OC₄H₉(n) | H | H | H | CH₂ | 1 | 142–145 |
| 5 | H | OCH₃ | H | H | CH₂ | 1 | 193–194 |
| 6 | OCH₃ | OCH₃ | H | H | CH₂ | 1 | 202–204 |
| 7 | H | —OCH₂O— | | H | CH₂ | 1 | 214–215 |
| 8 | H | OCH₂C₆H₅ | H | H | CH₂ | 1 | 197–200 |
| 9 | H | H | CH₃ | H | CH₂ | 1 | 166–168 |
| 10 | Cl | H | H | H | CH₂ | 1 | 237–242 |
| 11 | H | H | CH(CH₃)₂ | H | CH₂ | 1 | 161–163 |
| 12 | H | H | OCH₂C₆H₅ | H | CH₂ | 1 | 148–150 |
| 13 | H | OCH₂C₆H₅ | OCH₂C₆H₅ | H | CH₂ | 1 | 188–191 |
| 14 | OCH₃ | OCH₃ | H | H | CH₂ | 2 | 183–185 |
| 15 | H | OCH₃ | H | H | CH₂ | 2 | 107–109 |
| 16 | H | OCH₃ | OCH₃ | H | CH₂ | 2 | 170–173 |
| 17 | OCH₃ | H | H | H | CH₂ | 2 | 155–157 |
| 18 | H | H | OCH₃ | H | O | 2 | 166–168 |
| 19 | H | H | Cl | H | O | 2 | 198–201 |
| 20 | H | Cl | H | H | O | 2 | 210–213 |
| 21 | H | Cl | H | H | N—COCH₃ | 2 | 205–210 |
| 22 | H | H | H | Cl | N—COCH₃ | 2 | 186–188 |

TABLE 1-continued $$R^b \underset{R^c}{\overset{R^a}{\diagdown}} \underset{R^d}{\diagdown} \overset{X}{\diagdown} (CH_2)_m$$
(structure with NHCH₂—phenyl·HCl)

| Ref. No. | $R^a$ | $R^b$ | $R^c$ | $R^d$ | X | m | Melting Point(°C.) |
|---|---|---|---|---|---|---|---|
| 23 | H | H | H | H | CH₂ | 3 | 203–207 |
| 24 | H | H | H | OCH₃ | CH₂ | 1 | oil |

REFERENCE EXAMPLE 25

To a solution of 17 g of 1-benzylamino-5,6-dimethoxyindane hydrochloride in 300 ml of ethanol are added 10 g of potassium carbonate, 3.0 g of potassium iodide and 17 g of ethyl bromoacetate, and the mixture is refluxed for 8 hours. The ethanol is distilled off under reduced pressure, 500 ml of ice-water is added to the residue, and extraction with 500 ml of ethyl acetate is carried out. After the extract is washed with water and dried, the ethyl acetate is distilled off under reduced pressure. The residue is dissolved in 200 ml of ethanol. To the solution are added 5.0 g of sodium hydroxide and 10 ml of water, and the mixture is refluxed for 2 hours. Thereafter, the ethanol is evaporated under reduced pressure, and the residue is dissolved in 300 ml of water. The mixture is neutralized with acetic acid, and subjected to extraction with 300 ml of chloroform. After the extract is washed with water and dried, the chloroform is distilled off. To the residue are added 20 ml of 20% alcoholic hydrochloric acid and 200 ml of ethyl ether, and the mixture is allowed to stand. Collection of the crystalline precipitates by filtration gives 14 g of N-benzyl-N-(5,6-dimethoxy-1-indanyl)glycine hydrochloride as colorless needles. Melting point: 174°–177° C.

REFERENCE EXAMPLE 26–48

The compounds shown in Table 2 can be obtained in a similar reaction procedure to that described in Example 25, by employing, as the respective starting compounds, compounds shown in Table 1.

TABLE 2

(structure with HOOC—CH₂ and CH₂—phenyl on N, ·HCl)

| Ref. No. | $R^a$ | $R^b$ | $R^c$ | $R^d$ | X | m | Melting point(°C.) |
|---|---|---|---|---|---|---|---|
| 26 | OCH₃ | H | H | H | CH₂ | 1 | 190–193 |
| 27 | H | H | OCH₃ | H | CH₂ | 1 | 178–180 |
| 28 | OC₄H₉(n) | H | H | H | CH₂ | 1 | 170–174 |
| 29 | H | OCH₃ | H | H | CH₂ | 1 | 202–205 |
| 30 | OCH₃ | OCH₃ | H | H | CH₂ | 1 | 155–157 |
| 31 | H | —OCH₂O— | | H | CH₂ | 1 | 205–208 |
| 32 | H | OCH₂C₆H₅ | H | H | CH₂ | 1 | 162–164 |
| 33 | H | H | CH₃ | H | CH₂ | 1 | 171–173 |
| 34 | Cl | H | H | H | CH₂ | 1 | 182–184 |
| 35 | H | H | CH(CH₃)₂ | H | CH₂ | 1 | 188–191 |
| 36 | H | H | OCH₂C₆H₅ | H | CH₂ | 1 | 183–185 |
| 37 | H | OCH₂C₆H₅ | OCH₂C₆H₅ | H | CH₂ | 1 | 188–191 |
| 38 | OCH₃ | OCH₃ | H | H | CH₂ | 2 | 172–174 |
| 39 | H | OCH₃ | H | H | CH₂ | 2 | 197–202 |
| 40 | H | OCH₃ | OCH₃ | H | CH₂ | 2 | 175–178 |
| 41 | OCH₃ | H | H | H | CH₂ | 2 | 177–179 |
| 42 | H | H | OCH₃ | H | O | 2 | 161–165 |
| 43 | H | H | Cl | H | O | 2 | 158–160 |
| 44 | H | Cl | H | H | O | 2 | 150–155 |
| 45 | H | Cl | H | H | NCOCH₃ | 2 | 165–169 |
| 46 | H | H | H | Cl | NCOCH₃ | 2 | * |
| 47 | H | H | H | H | CH₂ | 3 | 178–183 |
| 48 | H | H | H | OCH₃ | CH₂ | 1 | * |

*Amorphous powder

REFERENCE EXAMPLE 49

N-Benzyl-N-(5,6-dimethoxy-1-indanyl)glycine hydrochloride (14 g) is dissolved in 300 ml of ethanol, 3.0 g of 5% palladium-carbon is added and catalytic reduction is carried out at ordinary temperature and pressure.

After absorption of the calculated amount of hydrogen, the catalyst is filtered off, and the ethanol is distilled off under reduced pressure. The residue is dissolved in 10 ml of water and adjusted to pH 7.0 with aqueous ammonia. The crystalline precipitates are collected by filtration, washed with a small amount of water, and dried, to give 8.0 g of N-(5,6-dimethoxy-1-indanyl)glycine as colorless needles. Melting point: 213°–216° C.

REFERENCE EXAMPLES 50–72

By using the compounds shown in Table 2 as the starting materials and carrying out a similar reaction to that of Reference Example 49, there can be obtained the compounds shown in Table 3. The products of Reference Examples 56 and 61 are prepared from the starting compounds of Reference Examples 32 and 37, respectively, by the same manner.

REFERENCE EXAMPLE 74

By using 1-amino-1,2,3,4-tetrahydronaphthalene as a starting material, and carrying out a similar procedure to that of Reference Example 73, there can be obtained N-(1,2,3,4-tetrahydro-1-naphthyl)glycine ethyl ester. Melting point: 164°–166° C.

REFERENCE EXAMPLE 75

N-(4-Methoxy-1-indanyl)glycine (4.0 g) is dissolved in 80 ml of 20% ethanolic hydrochloric acid, and the mixture is refluxed for 7 hours. Thereafter, the ethanol is distilled off under reduced pressure, 200 ml of water is added to the residue for dissolution thereof, and the solution is made alkaline with sodium hydrogen carbonate and extracted with 300 ml of ethyl acetate. The extract is washed with water, and dried, and thereafter the ethyl acetate is distilled off under reduced pressure to give 4.0 g of N-(4-methoxy-1-indanyl)glycine ethyl ester. This is converted to the hydrochloride in a conventional manner, which occurs as colorless needles. Melting point: 167°–169° C.

TABLE 3

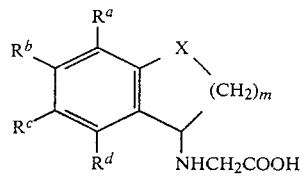

| Ref. No. | $R^a$ | $R^b$ | $R^c$ | $R^d$ | X | m | Melting point (°C.) |
|---|---|---|---|---|---|---|---|
| 50 | OCH$_3$ | H | H | H | CH$_2$ | 1 | 218–200 |
| 51 | H | H | OCH$_3$ | H | CH$_2$ | 1 | 184–188 |
| 52 | OC$_4$H$_9$(n) | H | H | H | CH$_2$ | 1 | 225–228 |
| 53 | H | OCH$_3$ | H | H | CH$_2$ | 1 | 205–208 |
| 54 | OCH$_3$ | OCH$_3$ | H | H | CH$_2$ | 1 | 215–217 |
| 55 | H | —OCH$_2$O— | | H | CH$_2$ | 1 | 227 |
| 56 | H | OH | H | H | CH$_2$ | 1 | 187–191 |
| 57 | H | H | CH$_3$ | H | CH$_2$ | 1 | 226 |
| 58 | Cl | H | H | H | CH$_2$ | 1 | 213–216* |
| 59 | H | H | CH(CH$_3$)$_2$ | H | CH$_2$ | 1 | 224 |
| 60 | H | H | OCH$_2$C$_6$H$_5$ | H | CH$_2$ | 1 | 205–209 |
| 61 | H | OH | OH | H | CH$_2$ | 1 | 215 |
| 62 | OCH$_3$ | OCH$_3$ | H | H | CH$_2$ | 2 | 180–182 |
| 63 | H | OCH$_3$ | H | H | CH$_2$ | 2 | 232–234 |
| 64 | H | OCH$_3$ | OCH$_3$ | H | CH$_2$ | 2 | 205–208 |
| 65 | OCH$_3$ | H | H | H | CH$_2$ | 2 | 229–233 |
| 66 | H | H | OCH$_3$ | H | O | 2 | 256–258* |
| 67 | H | H | Cl | H | O | 2 | 218–220* |
| 68 | H | Cl | H | H | O | 2 | 263–266* |
| 69 | H | Cl | H | H | NCOCH$_3$ | 2 | ** |
| 70 | H | H | H | Cl | NCOCH$_3$ | 2 | ** |
| 71 | H | H | H | H | CH$_2$ | 3 | 234–235 |
| 72 | H | H | H | OCH$_3$ | CH$_2$ | 1 | ** |

*Melting point of HCl salt
**Amorphous powder

REFERENCE EXAMPLE 73

To a solution of 13.3 g of 1-indanamine in 100 ml of methanol are added 6.9 g of potassium carbonate and 16.9 g of ethyl bromoacetate, and the mixture is refluxed for 30 minutes. The reaction mixture is poured into 300 ml of ice-water, and subjected to extraction with 500 ml of ethyl acetate. The extract is washed with water, dried, and concentrated under reduced pressure, and the residue is subjected to silica gel column chromatography and eluted with acetone-benzene (1:20) to give 9.0 g of N-(1-indanyl) glycine ethyl ester as a colorless oil. To this oil are added 5 ml of 20% alcoholic hydrochloric acid and 200 ml of ethyl ether, and the mixture is allowed to stand at room temperature to give 9.0 g of N-(1-indanyl)glycine ethyl ester hydrochloride as colorless needles. Melting point: 130°–132° C.

REFERENCE EXAMPLE 76

N-(1-Indanyl)glycine ethyl ester hydrochloride (9.0 g) is dissolved in 100 ml of 5N hydrochloric acid, and the mixture is refluxed for 4 hours. The reaction mixture is concentrated to dryness under reduced pressure, 10 ml of water is added to the residue, and the mixture is neutralized with aqueous ammonia. The resulting crystalline precipitates are collected by filtration, washed with water, and dried, to give 6.0 g N-(1-indanyl)glycine as colorless needles. Melting point: 184°–186° C.

REFERENCE EXAMPLE 77

By a procedure similar to that described in Reference Example 76, N-(1,2,3,4-tetrahydro-1-naphthyl)glycine ethyl ester hydrochloride gives N-(1,2,3,4-tetrahydro-1-naphthyl)glycine. Melting point: 227° C.

REFERENCE EXAMPLE 78

To a solution of 10 g of 1-indanamine in 200 ml of ethanol are added 6.0 g of potassium carbonate and 14.8 g of ethyl 2-bromopropionate, and the mixture is refluxed for 5 hours. The reaction mixture is concentrated under reduced pressure, then 300 ml of ice-water is added, and extraction is carried out with 200 ml of ethyl acetate. The extract is washed with water and dried, thereafter the ethyl acetate is distilled off under reduced pressure, 10 ml of 20% alcoholic hydrochloric acid and 100 ml of ethyl ether are added to the residue, and the mixture is allowed to stand at room temperature. The crystalline precipitates are collected by filtration and dried to give 9.5 g of N-(1-indanyl)alanine ethyl ester hydrochloride as colorless needles melting at 172°–174° C.

REFERENCE EXAMPLE 79

N-(1-Indanyl)alanine ethyl ester hydrochloride (9.0 g) is dissolved in 100 ml of 5N hydrochloric acid, and the mixture is refluxed for 3 hours. The reaction mixture is concentrated to dryness under reduced pressure, 10 ml of water is added to the residue, and the mixture is neutralized with aqueous ammonia. The resulting crystalline precipitates are collected by filtration, washed with water, and dried, to give 5.8 g of N-(1-indanyl)alanine as colorless scales. Melting point: 248°–250° C.

REFERENCE EXAMPLE 80

N-Benzyl-N-(6-benzyloxy-1-indanyl)glycine hydrochloride (9.5 g) obtained in the Reference Example 36 is dissolved in 200 ml of ethanol, and catalytically reduced in the presence of 3.0 g of 5% palladium-carbon at ordinary temperature and pressure, thereafter the catalyst is filtered off, and the solvent is distilled off under reduced pressure. The residue is dissolved in 20 ml of water, and adjusted to pH 7.0 with aqueous ammonia. The resulting crystalline precipitates are collected by filtration, washed with a small amount of water and dried to give 6.0 g of N-(6-hydroxy-1-indanyl)glycine as colorless needles. Melting point: 260° C.

REFERENCE EXAMPLE 81

In a solution of 10 g of indan-2-one in 200 ml of methanol is dissolved 20 g of glycine ethyl ester hydrochloride, and 5.0 g of sodium cyanoborohydride is added portionwise under ice cooling and stirring. After stirring at room temperature for 2 hours, the reaction mixture is poured into 500 ml of ice-water, make alkaline with sodium hydrogen carbonate and subjected to extraction with 300 ml of ethyl acetate. The extract is washed with water and dried, thereafter the ethyl acetate is distilled off under reduced pressure, 10 ml of 20% alcoholic hydrochloric acid and 200 ml of ethyl ether are added to the residue, and the mixture is allowed to stand at room temperature. The resulting crystalline precipitates are collected by filtration and dried to give 11 g of N-(2-indanyl)glycine ethyl ester hydrochloride as colorless needles. Melting point: 165°–167° C.

REFERENCE EXAMPLE 82

By a procedure similar to that described in Reference Example 76, N-(2-indanyl)glycine ethyl ester hydrochloride gives N-(2-indanyl)glycine as colorless needles. Melting point: 211°–214° C.

REFERENCE EXAMPLE 83

By using 3,4-dihydro-2(1H)-naphthalenone and carrying out the reaction and treatment in a similar manner to that of Reference Example 1, there is obtained 2-benzylamino-1,2,3,4-tetrahydronaphthalene hydrochloride as colorless needles. Melting point: 245°–247° C.

REFERENCE EXAMPLE 84

By using 2-benzylamino-1,2,3,4-tetrahydronaphthalene hydrochloride and carrying out the reaction and treatment in a similar manner to that of Reference Example 25, there is obtained N-benzyl-N-(1,2,3,4-tetrahydro-2-naphthyl)glycine hydrochloride as colorless scales. Melting point: 128°–131° C.

REFERENCE EXAMPLE 85

By using N-benzyl-N-(1,2,3,4-tetrahydro-2-naphthyl)glycine hydrochloride and carrying out the reaction and treatment in a similar manner to that of Reference Example 49, there is obtained N-(1,2,3,4-tetrahydro-2-naphthyl)glycine. Colorless needles. Melting point: 223°–227° C.

REFERENCE EXAMPLE 86

By a procedure similar to that described in Reference Example 81, 5,6-dimethoxy-2-indane gives N-(5,6-dimethoxy-2-indanyl)glycine ethyl ester hydrochloride. Melting point: 225°–228° C.

REFERENCE EXAMPLE 87

By a procedure similar to that described in Reference Example 76, N-(5,6-dimethoxy-2-indanyl)glycine ethyl ester hydrochloride gives N-(5,6-dimethoxy-2-indanyl)glycine. Melting point: 250° C.

REFERENCE EXAMPLE 88

By a procedure similar to that described in Reference Example 81, 3,4-dihydro-2(1H)-naphthalenone gives N-(1,2,3,4-tetrahydro-2-naphthyl)glycine ethyl ester hydrochloride. Melting point: 198°–200° C.

REFERENCE EXAMPLE 89

By a procedure similar to that described in Reference Example 81, 7-methoxy-3,4-dihydro-2(1H)-naphthalenone gives N-(7-methoxy-1,2,3,4-tetrahydro-2-naphthyl)glycine ethyl ester hydrochloride. Melting point: 198°–200° C.

REFERENCE EXAMPLE 90

By a procedure similar to that described in Reference Example 76, N-(7-methoxy-1,2,3,4-tetrahydro-2-naphthyl)glycine ethyl ester hydrochloride gives N-(7-methoxy-1,2,3,4-tetrahydro-2-naphthyl)glycine. Melting point: 203° C.

REFERENCE EXAMPLE 91

By a procedure similar to that described in Reference Example 81, 6-methoxy-3,4-dihydro-2(1H)-naphthalenone gives N-(6-methoxy-1,2,3,4-tetrahydro-2-naphthyl)glycine ethyl ester hydrochloride. Melting point: 188°–190° C.

REFERENCE EXAMPLE 92

By a procedure similar to that described in Reference Example 81, N-(6-methoxy-3,4-dihydro-2-naphthyl)glycine ethyl ester hydrochloride gives N-(6-methoxy-1,2,3,4-tetrahydro-2-naphthyl)glycine. Melting point: 195°–198° C.

REFERENCE EXAMPLE 93

By a procedure similar to that described in Reference Example 81, 2-indanone and L-alanine methyl ester hydrochloride give N-(2-indanyl)-L-alanine methyl ester hydrochloride. Melting point: 215° C.

REFERENCE EXAMPLE 94

By a procedure similar to that described in Reference Example 76, N-(2-indanyl)-L-alanine methyl ester hydrochloride gives N-(2-indanyl)-L-alanine. Melting point: 285° C.

EXAMPLE 1

N-(6-Methoxy-1-indanyl)glycine (2.0 g) is suspended in 20 ml of dimethylacetamide, then 2.2 g of 3-acetylthio-2-methylpropionyl chloride is added dropwise with stirring at room temperature, and thereafter stirring is continued at room temperature for 2 hours. The reaction mixture is poured into 200 ml of water, and extracted with 200 ml of ethyl acetate. The extract is washed with 20 ml of 10% hydrochloric acid and with water, and dried over anhydrous sodium sulfate. After ethyl acetate is distilled off under reduced pressure, the residue is subjected to silica gel column chromatography, eluted with acetone-benzene (1:9). The oily substance obtained is crystallized from an ethyl ether-petroleum ether mixture, to give 1.8 g of N-(3-acetylthio-2-methylpropionyl)-N-(6-methoxy-1-indanyl)glycine, colorless needles showing a melting point of 106°–110° C.

EXAMPLE 2

N-(6-Methoxy-1,2,3,4-tetrahydro-1-naphthyl)glycine (3.0 g) is suspended in 30 ml of dimethylacetamide, then 3.3 g of 3-acetylthio-2-methylpropionyl chloride is added dropwise with stirring at room temperature, and thereafter stirring is continued at room temperature for 2 hours. The reaction mixture is poured into 200 ml of water, and extracted with 200 ml of ethyl acetate. The extract is washed with 20 ml of 10% hydrochloric acid and with water, and dried over anhydrous sodium sulfate. Ethyl acetate is distilled off under reduced pressure, 10 ml of ethyl ether is added to the residue, and the mixture is allowed to stand at room temperature. Collection of the resulting crystalline precipitate by filtration gives 1.9 g of N-(3-acetylthio-2-methylpropionyl)-N-(6-methoxy-1,2,3,4-tetrahydro-1-naphthyl)glycine as colorless needles. Melting point: 158°–161° C.

EXAMPLES 3–25

By using the N-substituted glycines obtained in the corresponding Reference Examples as a starting material, and carrying out the reaction and treatment in a similar manner to that of Example 1 or 2, there can be obtained the compounds shown in Table 4.

TABLE 4

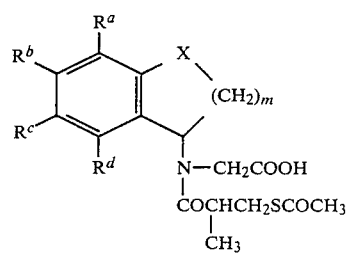

| (Ex.) No. | $R^a$ | $R^b$ | $R^c$ | $R^d$ | X | m | Melting point (°C.) |
|---|---|---|---|---|---|---|---|
| 3 | H | H | H | H | $CH_2$ | 1 | 102–104 |
| 4 | $OCH_3$ | H | H | H | $CH_2$ | 1 | * |
| 5 | H | $OCH_3$ | H | H | $CH_2$ | 1 | 137–142 |
| 6 | H | OH | H | H | $CH_2$ | 1 | 154–160 |
| 7 | $OCH_3$ | $OCH_3$ | H | H | $CH_2$ | 1 | 123–128 |
| 8 | H | $OCH_3$ | $OCH_3$ | H | $CH_2$ | 1 | 133–135 |
| 9 | H | —$OCH_2O$— | | H | $CH_2$ | 1 | 143–148 |
| 10 | $OC_4H_9(n)$ | H | H | H | $CH_2$ | 1 | * |
| 11 | Cl | H | H | H | $CH_2$ | 1 | 134–136 |
| 12 | H | OH | OH | H | $CH_2$ | 1 | * |
| 13 | H | H | $CH_3$ | H | $CH_2$ | 1 | 158–161 |
| 14 | H | H | $CH(CH_3)_2$ | H | $CH_2$ | 1 | 120–126 |
| 15 | H | H | $OCH_2C_6H_5$ | H | $CH_2$ | 1 | * |
| 16 | H | H | H | H | $CH_2$ | 2 | 125–128 |
| 17 | $OCH_3$ | H | H | H | $CH_2$ | 2 | 172–174 |
| 18 | $OCH_3$ | $OCH_3$ | H | H | $CH_2$ | 2 | 138–140 |
| 19 | H | $OCH_3$ | $OCH_3$ | H | $CH_2$ | 2 | 147–150 |
| 20 | H | H | $OCH_3$ | H | O | 2 | * |
| 21 | H | H | Cl | H | O | 2 | * |
| 22 | H | Cl | H | H | O | 2 | * |
| 23 | H | Cl | H | H | $NCOCH_3$ | 2 | * |
| 24 | H | H | H | Cl | $NCOCH_3$ | 2 | * |
| 25 | H | H | H | H | $CH_2$ | 3 | * |
| 26 | H | H | OH | H | $CH_2$ | 1 | 144–147 |

TABLE 4-continued

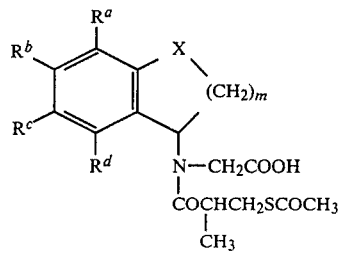

| (Ex.) No. | $R^a$ | $R^b$ | $R^c$ | $R^d$ | X | m | Melting point (°C.) |
|---|---|---|---|---|---|---|---|
| 27 | H | H | H | $OCH_3$ | $CH_2$ | 1 | 152–155 |

*The asterisked compounds are all obtained as amorphous colorless powder and do not show definite melting points.
Elemental analyses as well as characteristic absorptions in NMR (nuclear magnetic resonace) spectra and mass spectra, which provide the grounds for structure confirmation, are as follows:

The object compound in Example 4

Elemental Analysis for $C_{18}H_{23}O_5S$ Calcd: C, 59.18; H, 6.33; N, 3.83. Found: C, 59.11; H, 6.52; N, 3.81.

NMR Spectrum (CDCl$_3$) δ: 1.15–1.30(3H,d,CH$_3$C), 2.25–2.30 (3H,d,SCOCH$_3$), 3.70(3H,s,OCH$_3$), 5.60(1H,t,CH), 6.70–6.83(2H,m,ph), 10.25(1H,s,COOH)

In the above data, ph means phenyl protons, s singlet, d doublet, t triplet, q quartet, m multiplet and br broad absorption. (The same shall apply hereinafter.)

Mass Spectrum m/e: 365(M+), 322(M—COCH$_3$),

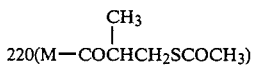

The object compound in Example 10

Elemental Analysis for $C_{21}H_{29}NO_5S \cdot \frac{1}{2}H_2O$ Calcd.: C, 60.32; H, 7.26; N, 3.36. Found: C, 60.35; H, 7.21; N, 3.59.

NMR Spectrum (CDCl$_3$) δ: 0.96(3H,t,CH$_3$), 1.20–1.33(3H,m,CH$_3$), 2.30(3H,d,SCOCH$_3$), 5.60(1H,t,CH), 6.65–6.68 (2H,m,ph), 10.13(1H,s,COOH)

Mass Spectrum m/e: 407(M+), 363(M—COCH$_3$), $$262(M-\overset{\overset{\displaystyle CH_3}{|}}{CO}CHCH_2SCOCH_3)$$

The object compound is Example 12

Elemental Analysis for $C_{17}H_{21}NO_6S \cdot \frac{1}{2}H_2O$ Calcd: C, 54.24; H, 5.89; N, 3.72. Found: C, 54.70; H, 6.19; N, 3.64.

NMR Spectrum (DMSO-d$_6$) δ: 1.20(3H,m,CH$_3$), 2.30(3H,d,CH$_3$COS), 5.40(1H,t,CH), 6.70(1H,s,ph), 6.90(1H,s,ph), 11.0–11.3(1H,br,COOH)

Mass Spectrum m/e: 376(M+), 323(M—COCH$_3$),

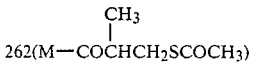

The object compound in Example 15

Elemental Analysis for $C_{24}H_{27}NO_5S \cdot \frac{1}{2}H_2O$ Calcd: C, 64.00; H, 6.26; N, 3.10. Found: C, 64.05; H, 6.36; N, 3.09.

NMR Spectrum (CDCl$_3$) δ: 1.15–1.30(3H,m,CH$_3$), 2.25(3H,d,SCOCH$_3$), 5.00(2H,s,OCH$_2$), 5.50(1H,t,CH), 6.75–6.90 (2H,m,ph), 7.10–7.26(1H,m,ph), 7.33(5H,s,ph), 9.80(1H,s,COOH)

Mass Spectrum m/e: 441(M+), 398(M—COCH$_3$), $$296(M-\overset{\overset{\displaystyle CH_3}{|}}{CO}CHCH_2SCOCH_3)$$

The object compound in Example 20

Elemental Analysis for $C_{18}H_{23}NO_6S$ Calcd.: C, 56.68; H, 6.08; N, 3.67. Found: C, 56.39; H, 5.98; N, 3.83.

NMR Spectrum (CDCl$_3$+D$_2$O) δ: 1.2–1.4(3H,m,CH$_3$), 2.3–2.4(3H,m,SCOCH$_3$), 3.6–3.7(3H,m,OCH$_3$), 5.1–6.1 (1H,m,CH), 6.3–6.8(3H,m,ph)

Mass Spectrum m/e: 381(M+)

The object compound in Example 21

Elemental Analysis for $C_{17}H_{20}NO_5SCl$ Calcd.: C, 52.92; H, 5.23; N, 3.63. Found: C, 52.87; H, 5.42; N, 3.68.

NMR Spectrum (CDCl$_3$+D$_2$O) δ: 1.1–1.4(3H,m,CH$_3$), 2.3–2.4 (3H,m,SCOCH$_3$), 5.1–6.1(1H,m,CH), 6.7–7.2(3H,m,ph)

Mass Spectrum m/e: 385(M+),

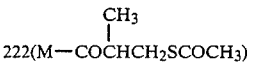

The object compound in Example 22

Elemental Analysis for $C_{17}H_{20}NO_5SCl$ Calcd: C, 52.92; H, 5.23; N, 3.63. Found: C, 52.98; H, 5.28; N, 3.78.

NMR Spectrum (CDCl$_3$+D$_2$O) δ: 1.1–1.4(3H,m,CH$_3$), 2.2–2.4(3H,m,SCOCH$_3$), 5.2–6.1(1H,m,CH), 6.7–7.1(3H,m,ph)

Mass Spectrum m/e: 385(M+), $$240(M-\overset{\overset{\displaystyle CH_3}{|}}{CO}CHCH_2SCOCH_3)$$

The object compound in Example 23

Elemental Analysis for $C_{19}H_{23}N_2O_5SCl$ Calcd.: C, 53.46; H, 5.43; N, 6.56. Found: C, 53.27; H, 5.68; N, 6.44.

NMR Spectrum (CDCl$_3$+D$_2$O), δ: 1.1–1.4(3H,m,CH$_3$), 2.1–2.4 (6H,m,SCOCH$_3$ and NCOCH$_3$), 5.2–6.0(1H,m,CH, 7.0–7.6 (3H,m,ph)

Mass Spectrum m/e: 426(M+),

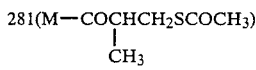
281(M—COCHCH₂SCOCH₃)
  |
  CH₃

The object compound in Example 24

Elemental Analysis for C₁₉H₂₃N₂O₅SCl.3/2H₂O Calcd.: C, 50.27; H, 5.77; N, 6.17. Found: C, 50.35; H, 5.38; N, 5.88.
NMR Spectrum (CDCl₃+D₂O) δ: 1.0–1.3(3H,m,CH₃), 2.3(3H,s,COCH₃), 2.4(3H,s,COCH₃), 5.4–5.8(1H,m,CH), 7.3–7.7(3H,m,ph)

The object compound in Example 25

Elemental Analysis for C₁₉H₂₅NO₄ Calcd.: C, 62.79; H, 6.93; N, 3.85. Found: C, 62.98; H, 7.18; N, 3.66.
NMR Spectrum (CDCl₃) δ: 1.15–1.30(3H,m,CH₃), 2.30(3H,d,SCOCH₃), 5.25–6.25(1H,m,CH), 7.0–7.30(4H,m,ph), 8.65(1H,s,COOH)

By the same reaction procedure as described in Example 1 except for employing 3-acetylthiopropionyl chloride instead of 3-acetylthio-2-methylpropionyl chloride, the compounds of Examples 28 and 29 can be obtained as colorless amorphous powder.

EXAMPLE 28

N-(3-Acetylthiopropionyl)-N-(1-indanyl)glycine

Elemental Analysis for C₁₆H₁₉NO₄S Calcd.: C, 59.80; H, 5.96; N, 4.36. Found: C, 59.50; H, 6.25; N, 4.30.
NMR Spectrum (CDCl₃) δ: 2.3(3H,s,CH₃COS), 5.3–6.3(1H,m,CH), 7.0–7.3(4H,m,ph), 8.5(1H,s,COOH)
Mass Spectrum m/e: 321(M+), 190(M—COCH₂CH₂SCOCH₃)

EXAMPLE 29

N-(3-Acetylthiopropionyl)-N-(5,6-dimethoxy-1-indanyl)glycine

Elemental Analysis for C₁₈H₂₃NO₆S.½H₂O Calcd.: C, 55.38; H, 6.20; N, 3.59. Found: C, 55.48; H, 6.28; N, 3.62.
NMR Spectrum (CDCl₃) δ: 2.3(3H,s,COCH₃), 3.75(3H,s,CH₃O), 3.85(3H,s,CH₃O), 6.7(2H,s,ph), 7.4(1H,s,COOH)
Mass Spectrum m/e: 381(M+), 250(M—COCH₂CH₂SCOCH₃)

EXAMPLE 30

N-(1-Indanyl)alanine (3.0 g) is suspended in 30 ml of dimethylacetamide, then 3.3 g of 3-acetylthio-2-methylpropionyl chloride is added dropwise with stirring at room temperature, and thereafter stirring is continued at room temperature for 2 hours. The reaction mixture is poured into 200 ml of water, and extracted with 200 ml of ethyl acetate. The extract is washed with 10 ml of 10% hydrochloric acid and with water, and dried. The ethyl acetate is distilled off under reduced pressure, and the residue is crystallized from an ethyl ether-petroleum ether mixture, to give 2.3 g of N-(3-acetylthio-2-methylpropionyl)-N-(1-indanyl)alanine, colorless needles having a melting point of 133°–137° C.

EXAMPLE 31

N-(4-Methoxy-1-indanyl)glycine ethyl ester (3.0 g) is dissolved in 30 ml of dimethylacetamide, then 3.3 g of 3-acetylthio-2-methylpropionyl chloride is added dropwise with stirring at room temperature, and the mixture is stirred at room temperature for 2 hours. The reaction mixture is poured into 200 ml of water, and extracted with ethyl acetate. The extract is washed with 10 ml of 10% hydrochloric acid and with water and dried, and ethyl acetate is distilled off under reduced pressure. The residue is purified by subjecting to silica gel column chromatography eluted with acetone-benzene (1:20), to give 3.2 g of N-(3-acetylthio-2-methylpropionyl)-N-(4-methoxy-1-indanyl)glycine ethyl ester as a colorless oil.

Elemental Analysis for C₂₀H₂₇NO₅S Calcd.: C, 61.05; H, 6.92; N, 3.56. Found: C, 61.50; H, 6.93; N, 3.29.
NMR Spectrum (CDCl₃) δ: 1.23(3H,t,CH₃), 1.30(1H,s,CH₃), 2.33(3H,d,SCOCH₃), 3.85(3H,s,OCH₃), 4.10(2H,q,CH₂), 5.60(1H,t,CH), 6.70–6.90(2H,m,ph), 7.10–7.25(1H,m,ph)
Mass Spectrum m/e: 393(M+), 350(M—COCH₃),

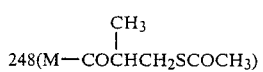
      CH₃
       |
248(M—COCHCH₂SCOCH₃)

EXAMPLE 32

By using N-(1,2,3,4-tetrahydro-2-naphthyl)glycine as a starting material, and carrying out the reaction and treatment in a similar manner to that of Example 2, there is obtained N-(3-acetylthio-2-methylpropionyl)-N-(1,2,3,4-tetrahydro-2-naphthyl)glycine as colorless amorphous powder.

Elemental Analysis for C₁₈H₂₃NO₄S.½H₂O Calcd.: C, 60.32; H, 6.75; N, 3.91. Found: C, 60.59; H, 6.75; N, 3.69.
NMR Spectrum (CDCl₃) δ: 1.20–1.30(3H,m,CH₃), 1.70–2.10 (2H,m), 2.20–2.33(3H,d,SCOCH₃), 2.70–3.25(7H,m), 3.95–4.40(3H,m), 7.06–7.20(4H,m,ph), 9.20(1H,s,COOH)
Mass Spectrum m/e: 349(M+), 306(M—COCH₃),

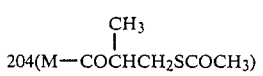
      CH₃
       |
204(M—COCHCH₂SCOCH₃)

EXAMPLE 33

By using N-(6-methoxy-1,2,3,4-tetrahydro-2-naphthyl) glycine as a starting material, and carring out the reaction and treatment in a similar manner to that of Example 2, there is obtained N-(3-acetylthio-2-methylpropionyl)-N-(6-methoxy-1,2,3,4-tetrahydro-2-naphthyl)glycine as colorless needles. Melting point: 118°–122° C.

EXAMPLE 34

By using N-(7-methoxy-1,2,3,4-tetrahydro-2-naphthyl)glycine as a starting material, and carrying out the reaction and treatment in a similar manner to that of Example 2, there is obtained N-(3-acetylthio-2-methylpropionyl)-N-(7-methoxy-1,2,3,4-tetrahydro-2-naphthyl)glycine as colorless needles. Melting point: 147°–150° C.

EXAMPLE 35

By using N-(2-indanyl)glycine as a starting material, and carrying out the reaction and treatment in a similar manner to that of Example 1, there is obtained N-(3-acetylthio-2-methylpropionyl)-N-(2-indanyl)glycine as colorless needles. Melting point: 81°–83° C.

EXAMPLE 36

By reacting N-(2-indanyl)glycine with 3-acetylthio-2(S)-methylpropionyl chloride in a similar manner to that of Example 35, there is obtained 3-acetylthio-2(S)-methylpropionyl)-N-(2-indanyl)glycine as colorless amorphous powder.

Elementary Analysis for $C_{17}H_{21}NO_4S$ Calcd.: C, 60.88; H, 6.31; N, 4.18. Found: C, 60.87; H, 6.32; N, 4.10. $[\alpha]_D^{22} -97.0°$ (c=0.965, MeOH).

EXAMPLE 37

N-(2-Indanyl)glycine (1.0 g) is suspended in 10 ml of dimethylacetamide, then 2.0 g of 3-benzoylthio-2-methylpropionyl chloride is added dropwise with stirring at room temperature, and thereafter stirring is continued at room temperature for 2 hours. The reaction mixture is poured into 100 ml of water, and extracted with 200 ml of ethyl acetate. The extract is washed with 20 ml of 10% hydrochloric acid and with water, and dried over anhydrous sodium sulfate. After ethyl acetate is distilled off under reduced pressure, the residue is subjected to silica gel column chromatography and eluted with acetone-benzene (1:9). The oil obtained is crystallized from an ethyl ether-petroleum ether mixture, to give 1.4 g of N-(3-benzoylthio-2-methylpropionyl)-N-(2-indanyl)glycine, colorless needles showing a melting point of 113°-115° C.

EXAMPLE 38

By reacting N-(2-indanyl)glycine with 3-benzoylthio-2(S)-methylpropionyl chloride in a similar manner to that of Example 37, there is obtained N-(3-benzoylthio-2(S)-methylpropionyl)-N-(2-indanyl)glycine. Colorless needles.

Melting point: 128°-129° C.
$[\alpha]_D^{21.5} -87.5°$ (c=1.18, MeOH)

EXAMPLE 39

By reacting N-(2-indanyl)glycine with 3-benzoylthio-2(R)-methylpropionyl chloride in a similar manner to that of Example 37, there is obtained N-(3-benzoylthio-2(R)-methylpropionyl)-N-(2-indanyl)glycine as colorless needles.

Melting point: 127°-129° C.
$[\alpha]_D^{21.5} +85.8°$ (c=1.55, MeOH)

EXAMPLE 40

By reacting N-(2-indanyl)glycine with 3-acetylthiopropionyl chloride in a similar manner to that of Example 1, there is obtained N-(3-acetylthiopropionyl)-N-(2-indanyl)glycine as colorless scales.

Melting point: 120°-122° C.

EXAMPLE 41

By treating N-(5,6-dimethoxy-2-indanyl)glycine in a similar manner to that of Example 1, there is obtained N-(3-acetylthio-2-methylpropionyl)-N-(5,6-dimethoxy-2-indanyl)glycine. Colorless needles. Melting point: 135°-137° C.

EXAMPLE 42

By treating N-(2-indanyl)-L-alanine in a similar manner to that of Example 30, there is obtained N-(3-acetylthio-2-methylpropionyl)-N-(2-indanyl)-L-alanine. Colorless scales. Melting point: 140°-142° C.

EXAMPLE 43

N-(5,6-Dimethoxy-1-indanyl)glycine (4.0 g) is suspended in 40 ml of dimethylacetamide, then 4.4 g of 3-acetylthio-2-acetylthiomethylpropionyl chloride is added dropwise with stirring at room temperature, and the mixture is stirred at room temperature for 2 hours. The reaction mixture is poured into 400 ml of water and extracted with 300 ml of ethyl acetate. The extract is washed with 30 ml of 10% hydrochloric acid and with water, and dried. After ethyl acetate is distilled off under reduced pressure, ethyl ether is added to the residue and the mixture is allowed to stand at room temperature. The resulting crystalline precipitates are collected by filtration to give 3.4 g of N-(3-acetylthio-2-acetylthiomethylpropionyl)-N-(5,6-dimethoxy-1-indanyl)glycine as colorless needles melting at 140°-143° C.

EXAMPLE 44

By treating N-(2-indanyl)glycine in a similar manner to that of Example 43, there is obtained N-(3-acetylthio-2-acetylthiomethylpropionyl)-N-(2-indanyl)glycine as colorless needles. Melting point: 114°-115° C.

EXAMPLE 45

N-(3-Acetylthio-2-methylpropionyl)-N-(5,6-dimethoxy-1-indanyl)glycine (1.0 g) is dissolved in 50 ml of 5.5N methanolic ammonia, and the mixture is stirred at room temperature for 2 hours. The reaction mixture is concentrated at 40° C. under reduced pressure, and the residue is dissolved in 10 ml of water, made acidic with 10% hydrochloric acid, and extracted with 200 ml of ethyl acetate. The extract is washed with water, dried, and then treated with activated carbon. After ethyl acetate is distilled off under reduced pressure, a mixture of ethyl ether and petroleum ether is added to the residue to give 6.6 g of N-(3-mercapto-2-methylpropionyl)-N-(5,6-dimethoxy-1-indanyl)glycine as colorless powder.

Elemental Analysis for $C_{17}H_{23}NO_5S \cdot \frac{1}{2}H_2O$ Calcd.: C, 56.34; H, 6.68; N, 3.87. Found: C, 56.68; H, 6.68; N, 3.88.

NMR Spectrum (CDCl$_3$) δ: 1.20–1.40(3H,m,CH$_3$), 3.80(6H,s,OCH$_3$), 5.60(1H,t,CH), 6.70(1H,s,ph), 6.85(1H,ph), 9.50(1H,s,COOH)

Mass Spectrum m/e: 353(M$^+$), 294(M—CH$_2$COOH),

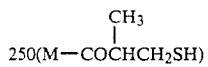
250(M—COCHCH$_2$SH)

EXAMPLE 46

By a reaction procedure similar to that described in Example 45, there is obtained N-(3-mercapto-2-methylpropionyl)-N-(5,6-methylenedioxy-1-indanyl)glycine as colorless amorphous powder from N-(3-acetylthio-2-methylpropionyl)-N-(5,6-methylenedioxy-1-indanyl)glycine.

Elemental Analysis for $C_{16}H_{19}NO_5S$ Calcd: C, 56.79; N, 5.88; N, 4.15. Found: C, 56.47; H, 5.71; N, 4.26.

NMR Spectrum (CDCl$_3$) δ: 1.20–1.30(3H,m,CH$_3$), 2.70–3.32(7H,m), 3.50–4.20(2H,m), 5.50(1H,t), 5.90(2H,s,—OCH$_2$O—), 6.68(2H,s,ph), 9.60(1H,s,COOH)

Mass Spectrum m/e: 337(M+), 234(M—COCH(CH₃)CH₂SH)

EXAMPLE 47

By a reaction procedure similar to that described in Example 45, there is obtained N-(3-mercapto-2-methylpropionyl)-N-(6-methoxy-2-indanyl)glycine as colorless amorphous powder from N-(3-acetylthio-2-methylpropionyl)-N-(6-methoxy-2-indanyl)glycine.

Elemental Analysis for $C_{16}H_{21}NO_4S$ Calcd.: C, 59.43; H, 6.55; N, 4.33. Found: C, 59.64; H, 6.60; N, 4.25.

NMR Spectrum (CDCl₃) δ: 1.10–1.35(3H,m,CH₃), 2.30–3.30(7H,m), 3.30–4.15(2H,m), 3.70(3H,s,OCH₃), 5.40–5.80(1H,m), 6.70–7.20(3H,m,ph), 9.85(1H,s,COOH)

Mass Spectrum (m/e): 323(M+), 220(M—COCH(CH₃)CH₂SH)

EXAMPLE 48

By a reaction procedure similar to that described in Example 45, there is obtained N-(3-mercapto-2-methylpropionyl)-N-(1,2,3,4-tetrahydro-1-naphthyl)glycine as colorless amorphous powder from N-(3-acetylthio-2-methylpropionyl-N-(1,2,3,4-tetrahydro-1-naphthyl)glycine.

Elemental Analysis for $C_{16}H_{21}NO_3S$ Calcd.: C, 62.52; H, 6.88; N, 4.56. Found: C, 62.70; H, 6.57; N, 4.60.

NMR Spectrum (CDCl₃) δ: 1.15–1.30(3H,m,CH₃), 1.60–2.60(3H,m), 2.90–3.10(6H,m), 4.00(2H,s,CH₂—COOH), 4.10–4.25(1H,m), 7.20(4H,s,ph), 9.00(1H,s,COOH)

Mass Spectrum (m/e): 307(M+), 204(M—COCH(CH₃)CH₂SH)

EXAMPLE 49

By a reaction procedure similar to that described in Example 45, there is obtained N-(3-mercapto-2-methylpropionyl)-N-(7-methoxy-1,2,3,4-tetrahydro-2-naphthyl)glycine as colorless amorphous powder from N-(3-acetyl-2-methylpropionyl)-N-(7-methoxy-1,2,3,4-tetrahydro-2-naphthyl)glycine.

Elemental Analysis, for $C_{17}H_{23}NO_4S \cdot \frac{1}{2}H_2O$ Calcd.: C, 58.95; H, 6.98; N, 4.04. Found: C, 58.89; H, 6.93; N, 4.02.

NMR Spectrum (CDCl₃) δ: 1.15–1.30(3H,m,CH₃), 1.50–2.20(3H,m), 2.80–3.15(6H,m), 3.70(3H,s,OCH₃), 4.05(2H,s,—CH₂COOH), 4.10–4.30(1H,m), 6.60–7.05(3H,m,ph), 9.30(1H,s,COOH)

Mass Spectrum m/e: 337(M+), 234(M—COCH(CH₃)CH₂SH)

EXAMPLE 50

By a reaction procedure similar to that described in Example 45, there is obtained N-(3-mercapto-2-methylpropionyl)-N-(2-indanyl)glycine as colorless amorphous powder from N-(3-acetylthio-2-methylpropionyl)-N-(2-indanyl)glycine.

Elemental Analysis for $C_{15}H_{19}NO_3S$ Calcd.: C, 61.42; H, 6.53; N, 4.78. Found: C, 60.96; H, 6.69; N, 4.56.

NMR Spectrum (CDCl₃) δ: 1.20–1.30(3H,d,CH₃), 2.40–3.50(8H,m), 3.95(2H,s,CH₂COOH), 4.90–5.05(1H,m), 7.20(4H,s,ph), 9.05(1H,s,COOH)

Mass Spectrum m/e: 293(M+), 190(M—COCH(CH₃)CH₂SH)

EXAMPLE 51

By using N-(3-acetylthio-2-acetylthiomethylpropionyl)-N-(5,6-dimethoxy-1-indanyl)glycine as a starting material, and carrying out the reaction and treatment in a similar manner to that of Example 45, there is obtained N-(3-mercapto-2-mercaptomethylpropionyl)-N-(5,6-dimethoxy-1-indanyl)glycine as colorless powder.

Elemental Analysis for $C_{17}H_{23}NO_5S_2$ Calcd.: C, 52.98; H, 6.02; N, 3.64 Found: C, 52.72; H, 5.76; N, 3.58

NMR Spectrum (CDCl₃) δ: 4.80(3H,s,OCH₃), 3.90(3H,s,OCH₃), 5.65(1H,t,CH), 6.70(1H,ph), 6.85(1H,ph), 9.80(1H,s,COOH)

Mass Spectrum m/e: 385(M+), 383(M—H₂), 250(M—CO(CH₂SH)₂)

EXAMPLE 52

N-(3-Mercapto-2-mercaptomethylpropionyl)-N-(5,6-dimethoxy-1-indanyl)glycine (1 g) is dissolved in 20 ml of ethanol, and a 5% iodine solution in ethanol is added dropwise with ice cooling and stirring. When the color of iodine does not fade any more, the dropping is discontinued, the reaction mixture is poured into 100 ml of water and extracted with ethyl acetate, the extract is dried, and the solvent is then distilled off under reduced pressure. The residue is dissolved in ether, the insoluble substance is filtered off with a small amount of activated carbon, and ether is distilled off at room temperature under reduced pressure, to give 0.3 g of N-(5,6-dimethoxy-1-indanyl)-N-(1,2-dithiolane-4-carbonyl)glycine as a pale yellow viscous oil.

Elemental Analysis, for $C_{17}H_{21}NO_5S_2$ Calcd.: C, 53.28; H, 5.52; N, 3.65. Found: C, 53.20; N, 5.38; N, 3.71.

NMR Spectrum (CDCl₃) δ: 4.81(3H,s,OCH₃), 3.95(3H,s,OCH₃), 5.65(1H,t,CH), 6.74(1H,ph), 6.90(1H,ph), 9.65(1H,s,COOH)

Mass Spectrum m/e: 383(M+),

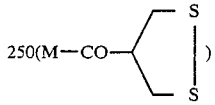

EXPERIMENT 1

Inhibitions of Angiotensin I Converting Enzyme by the Compounds of this Invention.

EXPERIMENTAL METHOD

The experiment was conducted in accordance with a modification of the method described by Cushman et al. [Biochemical Pharmacology, Vol. 20, p1637(1971)]. That is, using hippuryl-L-histidyl-L-leucine(HHL) as the substrate, the ACE (angiotensin I converting enzyme) inhibitory activity was determined in terms of percent inhibition on the amount of hippuric acid produced by ACE when the present compound was added. A solution of the compound of the present invention dissolved in a 0.02 to 2% dimethyl sulfoxide-500 mM potassium phosphate buffer solution (pH 8.3, containing 300 mM sodium chloride) was added to 100 μl of ACE (protein concentration, 20 mg/ml) and 100 μl of 1.25 mM HHL. In this experiment, a potassium phosphate buffer solution containing dimethyl sulfoxide at a concentration equal to that of the test solution was used as a control. After incubating the solution at 37° C. for one hour, 150 μl of 1N hydrochloric acid was added to the solution to terminate the reaction. After 1 ml of ethyl acetate was added, the solution was centrifuged at 3000 r.p.m. for 10 minutes. A 0.5 ml aliquot was separated from the ethyl acetate layer and dried at a temperature below 50° C. under nitrogen gas streams. The residue was mixed with 5 ml of 1M aqueous sodium chloride and the mixture was subjected to colorimetry at a wavelength of 228 nm.

TEST RESULT

The test results obtained with respect to the compounds of Examples 6, 21, 32, 38, 40, 43 and 45 are shown in Table 5 below.

TABLE 5

| Example No. of tested compound | Concentration (μm) | Inhibitory Activity on ACE (%) |
|---|---|---|
| 6 | 1 | 45 |
|  | 10 | 88 |
| 21 | 1 | 19 |
|  | 10 | 66 |
| 32 | 1 | 73 |
|  | 10 | 95 |
| 38 | 1 | 86 |
|  | 10 | 98 |
| 40 | 1 | 77 |
|  | 10 | 92 |
| 43 | 1 | 32 |
|  | 10 | 75 |
| 45 | 1 | 74 |
|  | 10 | 99 |

EXPERIMENT 2

Effect of Present Compounds against Hypertensive Activity of Angiotensin I

EXPERIMENT METHOD

Male rats (Sprague-Dawley) weighing 250 g to 350 g which were fed under free access to drinking water and feeds were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II, and then the tubes were fixed.

On the test day, an average blood pressure in the control phase was recorded on an electric hemodynamometer (MP-4T model manufactured by Nippon Koden, Japan) and thereafter angiotensin I and then angiotensin II were injected through the femoral vein at a dose of 300 ng/kg and 100 ng/kg respectively, to measure the hypertensive activity. Then, 13.8 μM/kg of the compound of this invention was administered orally as an aqueous solution or an aqueous gum arabic suspension, and 20, 60 and 120 minutes after the administration, angiotensin I and II were injected repeatedly to trace hypertensive reactions. In calculating the percent inhibition to the hypertensive acitivity of angiotensin I, the percent inhibitory value was corrected based on the variation with time in the hypertensive reaction by angiotensin II.

TEST RESULT

The test results obtained with respect to the compounds of Examples 1, 3, 8, 9, 18, 35 and 41 are shown in Table 6 below.

TABLE 6

| Example No. of Tested Compound | Percent Inhibition (%) against Hypertensive Reaction by Angiotensin I | | |
|---|---|---|---|
|  | After 20 min. | After 60 min. | After 120 min. |
| 1 | 96 | 94 | 91 |
| 3 | 95 | 90 | 83 |
| 8 | 86 | 94 | 91 |
| 9 | 81 | 78 | 59 |
| 18 | 83 | 70 | 72 |
| 35 | 100 | 100 | 91 |
| 41 | 89 | 93 | 92 |

PREPARATION EXAMPLE

The compounds (I) of the present invention are used, for example, for the treatment of hypertension in the following examples of formulation.

| 1. Tablets | |
|---|---|
| (1) N—(3-Acetylthio-2-methyl-propionyl)-N—(2-indanyl)glycine | 10 g |
| (2) Lactose | 90 g |
| (3) Corn Starch | 29 g |
| (4) Magnesium Stearate | 1 g |
|  | 130 g for 1000 tablets |

The above ingredients (1), (2) and 17 g of corn starch are blended, and granulated using a paste prepared from 7 g of corn starch. Five grams of corn starch and the ingredient (4) are added to the resulting granules and the mixture is compressed by a tabletting machine to prepare 1000 tablets having a diameter 7 mm each containing 10 mg of the active ingredient (1).

| 2. Capsules | |
|---|---|
| (1) N—(3-Acetylthio-2-methyl-propionyl)-N—(1,2,3,4-tetrahydro-2-naphthyl)glycine | 10 g |
| (2) Lactose | 135 g |
| (3) Cellulose Fine Powder | 70 g |
| (4) Magnesium Stearate | 5 g |
|  | 220 g for 1000 capsules |

All of the above components are blended and encapsulated into Gelatin Capsule No. 3 (IX Japanese Pharmacopoiea) to prepare 1000 capsules each containing 10 mg of the active component (1).

| 3. Injectable Solution | |
|---|---|
| (1) N—(3-Mercapto-2-methylpropionyl)-N—(5,6-dimethoxy-1-indanyl)glycine | 10 g |
| (2) Sodium Chloride | 9 g |
| (3) Chlorobutanol | 5 g |
| (4) Sodium Bicarbonate | 1 g |

All of the above ingredients are dissolved in 1000 ml of distilled water and charged into 1000 brown ampules each containing 1 ml of the solution. The ampules are replaced with nitrogen gas and sealed. The entire preparation steps are conducted under sterile conditions.

What is claimed is:

1. A compound of the formula

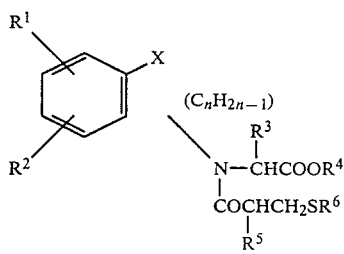

wherein

R¹ and R² independently represent hydrogen, halogen, $C_{1-4}$alkyl, hydroxyl, $C_{1-4}$alkyloxy or $C_{7-9}$aralkyloxy, or R¹ and R² jointly represent $C_{1-4}$alkylenedioxy;

R³ and R⁴ independently represent hydrogen or $C_{1-4}$alkyl;

R⁵ is hydrogen, $C_{1-4}$alkyl or —CH₂SR⁷ wherein R⁷ is hydrogen, $C_{2-4}$alkanoyl or benzoyl;

R⁶ is hydrogen, $C_{2-4}$alkanoyl or benzoyl, or R⁶ and R⁷ join to form a single bond;

X is —O— and n is 2, 3 or 4, or a pharmaceutically acceptable salt thereof.

2. A compound according to claim 1, wherein R¹ and R² independently represent hydrogen, halogen or $C_{1-4}$alkyloxy.

3. A compound according to claim 1, wherein R³ and R⁴ are hydrogen, and R⁵ is methyl.

4. A compound according to claim 1, wherein n is 3.

5. A compound according to claim 1, which is N-(3-acetylthio-2-methylpropionyl)-N-(6-methoxy-4-chromanyl)glycine.

6. The compound according to claim 1, which is N-(3-acetylthio-2-methylpropionyl)-N-(6-chloro-4-chromanyl)glycine.

7. A compound according to claim 1, which is N-(3-acetylthio-2-methylpropionyl)-N-(7-chloro-4-chromanyl)glycine.

8. A compound of the formula:

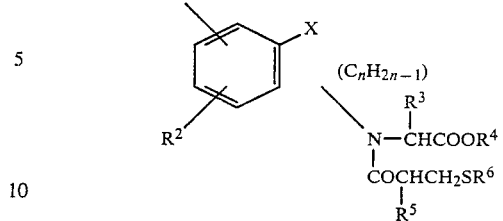

wherein

R¹ and R² independently represent hydrogen, halogen, $C_{1-4}$alkyl, hydroxyl, $C_{1-4}$alkyloxy or $C_{7-9}$aralkyloxy, or R¹ and R² jointly represent $C_{1-4}$alkylenedioxy, R³ and R⁴ independently represent hydrogen or $C_{1-4}$alkyl;

R⁵ is —CH₂SR⁷ and R⁶ and R⁷ jointly represent a single bond;

X is —CH₂—; and n is 2, 3 or 4, or a pharmaceutically acceptable salt thereof.

9. A compound according to claim 8, wherein R¹ and R² independently represent hydrogen or $C_{1-4}$alkyloxy.

10. A compound according to claim 8, wherein R³ and R⁴ are hydrogen and n is 2.

11. A compound according to claim 8, which is N-(5,6-dimethoxy-1-indanyl)-N-(1,2-dithiolane-4-carbonyl)glycine.

12. A compound of the formula:

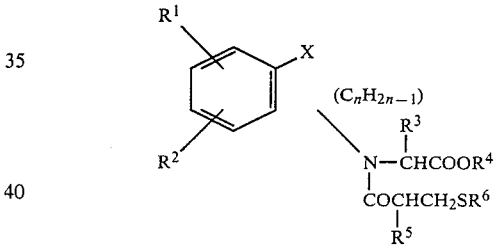

wherein

R¹ and R² jointly represent $C_{1-4}$alkylenedioxy, R³ and R⁴ independently represent hydrogen or $C_{1-4}$alkyl;

R⁵ is hydrogen, $C_{1-4}$alkyl or —CH₂—SR⁷ wherein R⁷ is hydrogen, $C_{2-4}$alkanoyl or benzoyl;

R⁶ is hydrogen, $C_{2-4}$alkanoyl or benzoyl;

X is —CH₂—; and n is 2, 3 or 4, or a pharmaceutically acceptable salt thereof.

13. A compound according to claim 12, wherein R³ and R⁴ are hydrogen, R⁵ is methyl and n is 2.

14. A compound according to claim 12, which is N-(3-acetylthio-2-methylpropionyl)-N-(5,6-methylenedioxy-1-indanyl)glycine.

15. A compound according to claim 12, which is N-(3-mercapto-2-methylpropionyl)-N-(5,6-methylenedioxy-1-indanyl)glycine.

* * * * *

UNITED STATES PATENT AND TRADEMARK OFFICE
CERTIFICATE OF CORRECTION

PATENT NO. : 4,521,607
DATED : June 4, 1985
INVENTOR(S) : Oka, et al.

It is certified that error appears in the above-identified patent and that said Letters Patent is hereby corrected as shown below:

Column 6, formula (VI) should read 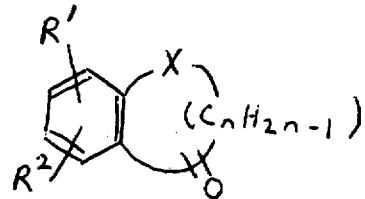

Column 6, formula (VIII) should read 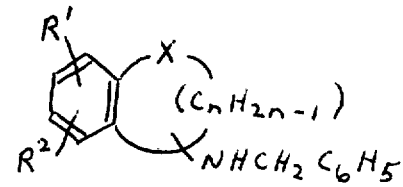

Column 6, formula (X) should read 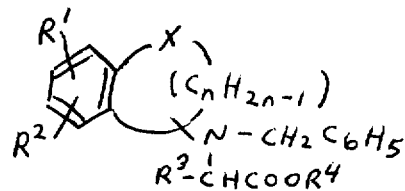

UNITED STATES PATENT AND TRADEMARK OFFICE
CERTIFICATE OF CORRECTION

PATENT NO. : 4,521,607
DATED : June 4, 1985
INVENTOR(S) : Oka, et al.

It is certified that error appears in the above—identified patent and that said Letters Patent is hereby corrected as shown below:

Column 6, formula (XI) should read

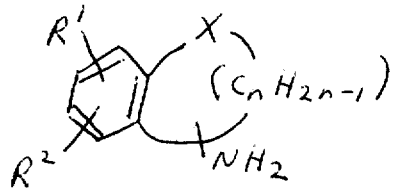

Column 27, the formula of claim 1 should read

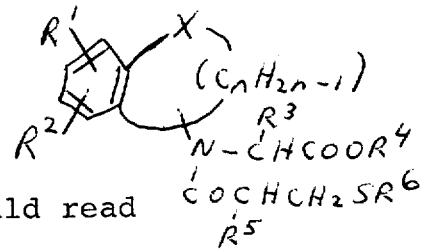

Column 28, the formula of claim 8 should read

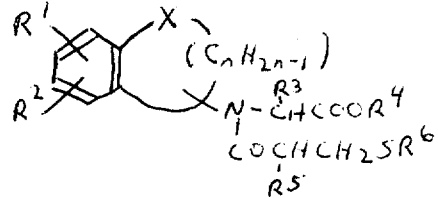

UNITED STATES PATENT AND TRADEMARK OFFICE
CERTIFICATE OF CORRECTION

PATENT NO. : 4,521,607

DATED : June 4, 1985

INVENTOR(S) : Oka, et al.

It is certified that error appears in the above-identified patent and that said Letters Patent is hereby corrected as shown below:

Column 28, the formula of claim 12 should read

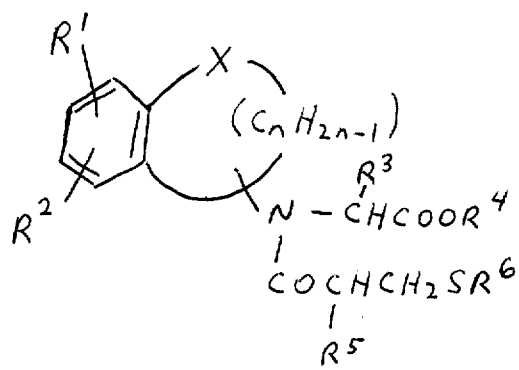

Signed and Sealed this

Third Day of December 1985

[SEAL]

Attest:

DONALD J. QUIGG

Attesting Officer     Commissioner of Patents and Trademarks